US012708418B2

(12) United States Patent
Sidebotham et al.

(10) Patent No.: US 12,708,418 B2
(45) Date of Patent: Aug. 18, 2026

(54) ORTHOPEDIC BONE SCREW

(71) Applicant: BioMedtrix, LLC, Whippany, NJ (US)

(72) Inventors: Christopher G. Sidebotham, Mendham, NJ (US); Gregory T. Van Der Meulen, Ketchum, ID (US)

(73) Assignee: BioMedtrix, LLC, Whippany, NJ (US)

( * ) Notice: Subject to any disclaimer, the term of this patent is extended or adjusted under 35 U.S.C. 154(b) by 128 days.

(21) Appl. No.: 18/475,657

(22) Filed: Sep. 27, 2023

(65) Prior Publication Data

US 2024/0099751 A1 Mar. 28, 2024

Related U.S. Application Data

(60) Provisional application No. 63/411,017, filed on Sep. 28, 2022.

(51) Int. Cl.
*A61B 17/86* (2006.01)
*A61B 17/56* (2006.01)

(52) U.S. Cl.
CPC ........ *A61B 17/8635* (2013.01); *A61B 17/863* (2013.01); *A61B 2017/564* (2013.01)

(58) Field of Classification Search
CPC .................................................. A61B 17/8635
See application file for complete search history.

(56) References Cited

U.S. PATENT DOCUMENTS 4,463,753 A 8/1984 Gustilo
5,615,575 A 4/1997 Goodwin
5,730,566 A 3/1998 Goodwin et al.
5,791,849 A 8/1998 Goodwin et al.
5,836,731 A 11/1998 Goodwin et al.
5,997,231 A 12/1999 Goodwin et al.
6,062,786 A 5/2000 Garver et al.
6,123,710 A 9/2000 Pinczewski et al.
6,162,001 A 12/2000 Goodwin et al.
6,561,741 B2 5/2003 Garver
9,644,660 B2 5/2017 Garver
9,644,663 B2 5/2017 Garver
9,644,664 B2 5/2017 Garver
9,644,665 B2 5/2017 Garver
10,555,758 B2 2/2020 Magee et al.

(Continued)

FOREIGN PATENT DOCUMENTS

CA 3072520 A1 4/2019
DE 102019115476 A1 12/2020

OTHER PUBLICATIONS

"Compact 2.0 LOCK Mandible: The Locking System for the Mandible," DePuy Synthes CMF, 2016 (28 pages).
"Flower Plate for Mediocarpal Partial Arthrodeses," Gebruder Martin GmbH & Co. KG, KLS Martin Group, 2017 (28 pages).
"MaxDrive: Oral and Maxillofacial Surgery," Gebruder Martin GmbH & Co. KG, KLS Martin Group, 2009 (12 pages).
"Set Scew Point Styles and their Uses," Atlantic Fasteners, 2014 (1 pages).

(Continued)

*Primary Examiner* — Olivia C Chang
(74) *Attorney, Agent, or Firm* — Klarquist Sparkman, LLP

(57) ABSTRACT

An orthopedic bone screw includes a head, and a shaft extending from the head and comprising threads. The threads have a major diameter and a minor diameter. The shaft includes a threadless atraumatic tip opposite the head, the threadless atraumatic tip having a cylindrical portion that is distal of the threads and a round end portion that is distal of the cylindrical portion and forms a tip of the orthopedic bone screw. A length of the cylindrical portion of the atraumatic tip is 25% to 150% of the major diameter of the threads.

22 Claims, 16 Drawing Sheets

(56) References Cited

U.S. PATENT DOCUMENTS

| | | | | |
|---|---|---|---|---|
| 10,893,897 | B2 | 1/2021 | Whipple et al. | |
| 10,918,430 | B2 | 2/2021 | Bottlang et al. | |
| 2006/0200151 | A1 | 9/2006 | Ducharme et al. | |
| 2007/0055249 | A1 | 3/2007 | Jensen et al. | |
| 2012/0130433 | A1 | 5/2012 | Huebner | |
| 2012/0283790 | A1 | 11/2012 | Meyer, III | |
| 2013/0211463 | A1 | 8/2013 | Mizuno et al. | |
| 2016/0235398 | A1 | 8/2016 | Nguyen et al. | |
| 2016/0310187 | A1 | 10/2016 | Leibinger et al. | |
| 2017/0209252 | A1 | 7/2017 | Ridgley et al. | |
| 2019/0008571 | A1* | 1/2019 | Roth | A61B 17/7035 |
| 2019/0239935 | A1 | 8/2019 | Willis et al. | |
| 2021/0140463 | A1 | 5/2021 | Garver | |
| 2021/0145492 | A1 | 5/2021 | Corrao, Jr. | |
| 2021/0196331 | A1* | 7/2021 | Muser | A61B 17/8635 |
| 2022/0249148 | A1* | 8/2022 | Hyer | A61B 17/7001 |

OTHER PUBLICATIONS

"Recos: Ulna Shortening and Radius Reconstruction System," Gebruder Martin GmbH & Co. KG, KLS Martin Group, 2019 (44 pages).

International Search Report and Written Opinion issued in related PCT Application No. PCT/US2023/075226 by Korean Intellectual Property Office as International Searching Authority on Jan. 16, 2024, 13 pages.

Communication pursuant to Rule 164(1) EPC issued in European Application No. 23873873.6 by the European Patent Office on Nov. 21, 2025 (12 pages).

Extended European Search Report mailed in European Patent Application No. 23873873.6 by the European Patent Office on Mar. 9, 2026, 13 pages.

* cited by examiner 300
310
Direction of Pullout
Direction of Insertion 300
310
Direction of Pullout
Direction of Insertion 333
335
310
300
305
Direction of Insertion
Direction of Pullout 333
335
310
300
305
Direction of Insertion
Direction of Pullout

ORTHOPEDIC BONE SCREW

CROSS REFERENCE TO RELATED APPLICATION

The present application claims the benefit of U.S. Provisional Application No. 63/411,017, filed Sep. 28, 2022, which is incorporated herein by reference in its entirety.

FIELD

The present disclosure pertains to orthopedic bone screws, such as self-tapping and/or locking cortical bone screws.

BACKGROUND

Bone screws are configured to be driven into holes prepared in one or a plurality of bones (or bone fragments) to repair a fracture, secure a bone plate to the bone, etc. Such holes are typically created using a drill. Existing bone screws can be angulated significantly around the opening of a pre-drilled hole in a bone, making it difficult to align the bone screw with the axis of the pre-drilled hole. This can make it difficult for self-tapping bone screws to initiate threading into the bone, and can also increase the risk of stress fracture due to misalignment between the bone screw and the hole axis. Existing self-tapping bone screws can also require relatively high torque and/or compressive force to initiate threading into a pre-drilled hole in a bone. Accordingly, a need exists for improvements to bone screws.

SUMMARY

The present disclosure pertains to orthopedic bone screws with atraumatic tips. In a representative example, an orthopedic bone screw comprises a head; and a shaft extending from the head and comprising threads, the threads comprising a major diameter and a minor diameter; the shaft comprising a threadless atraumatic tip opposite the head, the threadless atraumatic tip comprising a cylindrical portion that is distal of the threads, and a round end portion that is distal of the cylindrical portion and forms a tip of the orthopedic bone screw; wherein a length of the cylindrical portion of the atraumatic tip is 25% to 150% of the major diameter of the threads.

In another representative example, an orthopedic bone screw comprises a head; and a shaft extending from the head and comprising threads, the threads comprising a major diameter and a minor diameter; the shaft comprising a threadless atraumatic tip opposite the head, the threadless atraumatic tip comprising a cylindrical portion that is distal of the threads, and a round end portion that is distal of the cylindrical portion and forms a tip of the orthopedic bone screw; wherein at least the cylindrical portion of the threadless atraumatic tip comprises a plurality of cutting flutes.

In another representative example, an orthopedic bone screw comprises a head; a shaft extending from the head, the shaft comprising threads; the shaft comprising a threadless atraumatic tip opposite the head, the threadless atraumatic tip comprising a cylindrical portion and a round end portion distal of the cylindrical portion; wherein the threadless atraumatic tip has a length that is 50% to 100% of a diameter of the cylindrical portion of the threadless atraumatic tip.

The foregoing and other objects, features, and advantages of the disclosed technology will become more apparent from the following detailed description, which proceeds with reference to the accompanying figures.

BRIEF DESCRIPTION OF THE DRAWINGS

FIG. 5 is a side elevation view of the tip portion of the orthopedic bone screw of FIG. 1 with a curved surface of a cutting flute shown edge-on.

FIG. 6 is a side elevation view of the tip portion of the orthopedic bone screw of FIG. 1 rotated about its longitudinal axis relative to FIG. 5 to show a straight surface of the cutting flute edge-on.

FIG. 15 is a side elevation view of the tip portion of the orthopedic bone screw of FIG. 13 with a curved surface of a cutting flute shown edge-on.

FIG. 16 is a side elevation view of the tip portion of the orthopedic bone screw of FIG. 13 rotated about its longitudinal axis relative to FIG. 15 to show a straight surface of the cutting flute edge-on.

DETAILED DESCRIPTION

Explanation of Terms

Figure 1:
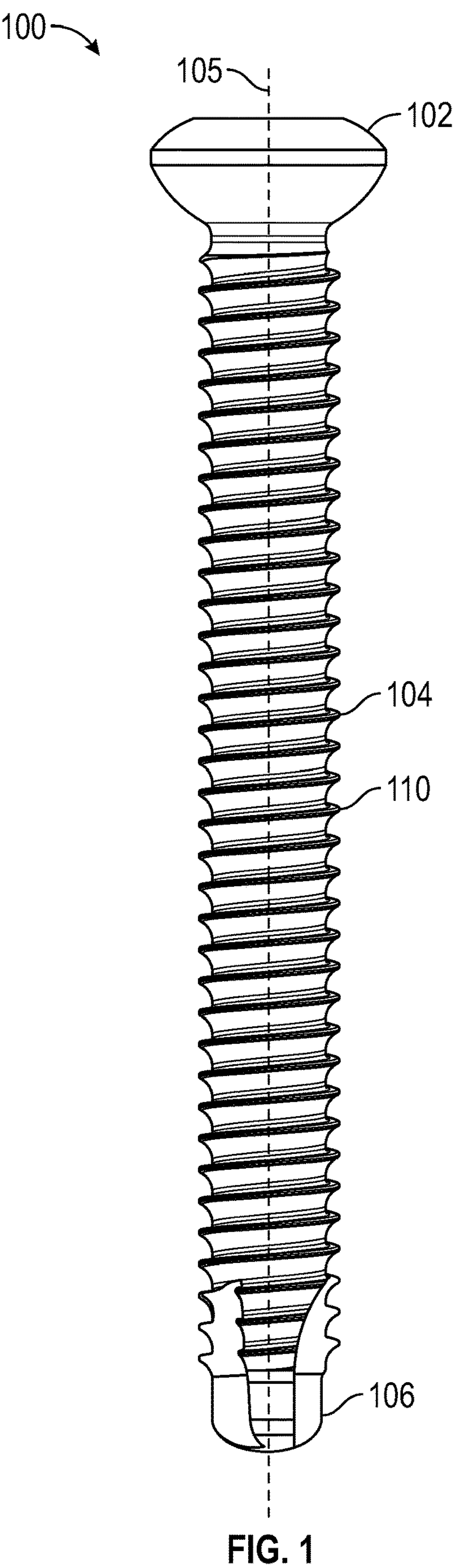
FIG. 1 is a side elevation view of an orthopedic bone screw, according to one example.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

As used in this disclosure and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Unless otherwise indicated, all numbers expressing angles, dimensions, quantities of components, forces, moments, percentages, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited.

Although there are alternatives for various components, dimensions, parameters, operating conditions, etc., set forth herein, that does not mean that those alternatives are necessarily equivalent and/or perform equally well. Nor does it mean that the alternatives are listed in a preferred order unless stated otherwise.

As used herein, values and/or relationships modified by the term "substantially" mean±10% of the stated value and/or relationship. "Substantially perpendicular" means an angle of 80° to 100° relative to a reference. "Substantially parallel" means an angle of ±10° relative to a reference.

Overview of the Disclosed Technology

The present disclosure pertains to bone screws for orthopedic surgical procedures. Bone screws are typically provided in two primary categories: cancellous bone screws configured for fixation in the soft, spongy interior or marrow of a bone, and cortical bone screws configured for fixation in the more dense, harder, exterior cortical bone. Cortical bone screws are typically configured as one of a locking bone screw or a non-locking bone screw. Locking bone screws can have threads incorporated into the head of the screw configured to engage corresponding threads formed in the inner diameter of a screw hole of a bone plate or other orthopedic fixation device. Bone screws can also be self-tapping, wherein the bone screw is configured to cut threads into the bone material as it is driven into the bone. Bone screws can also be non-self-tapping.

In certain examples, bone screws are configured to be driven into holes prepared in one or a plurality of bones (or bone fragments) to repair a fracture, secure a bone plate to the bone, etc. Such holes are typically created using a drill, and are referred to herein as "pre-drilled holes." Existing bone screws can be angulated significantly around the opening of a pre-drilled hole in a bone, making it difficult to align the bone screw with the axis of the pre-drilled hole. This can make it difficult to initiate threading of the bone screw into the bone, and can also increase the risk of stress fracture due to misalignment between the bone screw and the hole axis. Existing self-tapping bone screws can also require relatively high torque and/or compressive force to initiate threading into a pre-drilled hole in a bone.

The bone screw examples described herein include a variety of features that address the shortcomings of existing bone screws discussed above. For example, the bone screws described herein include a threadless atraumatic tip with a thread-free cylindrical portion and a rounded end portion. The threadless atraumatic tip can be received in a pre-drilled hole in a bone, and in some cases through a screw hole in a bone plate overlying the bone. The cylindrical portion of the threadless atraumatic tip can align the axis of the bone screw with the axis of the pre-drilled hole. This can enable the bone screw to be driven into the pre-drilled hole in the bone with a precise alignment. The length and diameter of the threadless atraumatic tip, and/or of the cylindrical portion of the atraumatic tip, can be sized such that when the bone screw is seated in a pre-drilled hole all or substantially all of the cutting flutes on the distal end of the bone screw are aligned and in contact with the surfaces of the pre-drilled hole. This can reduce the compressive force required to initiate threading of the bone screw into the bone.

Additionally, the design of the threadless atraumatic tip can reduce irritation of soft tissue. For example, the threadless atraumatic tip can include a thread runout region proximal of the cylindrical portion. Threads on the runout region can be sized and shaped in combination with the length of the cylindrical portion of the threadless atraumatic tip to minimize the length of threads that are exposed beyond the exit opening of the pre-drilled hole and in contact with soft tissue after the bone screw is driven into a bone. The smooth, rounded end surface of the atraumatic tip can also reduce irritation of soft tissue and associated post-operative complications.

Example 1: Orthopedic Bone Screw with Threadless Atraumatic Tip

Figure 2:
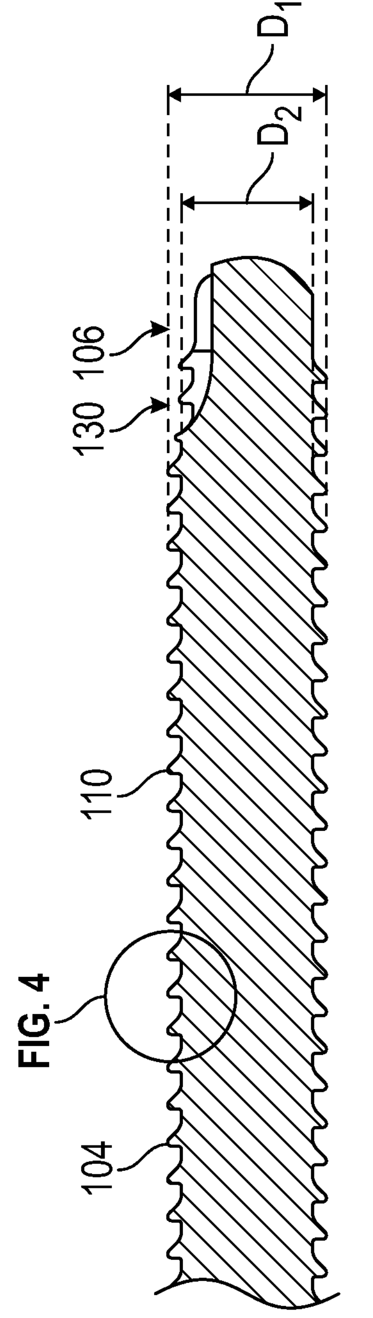
FIG. 2 is a cross-sectional view of a screw tip portion and shaft of the orthopedic bone screw of FIG. 1.
Figure 3:
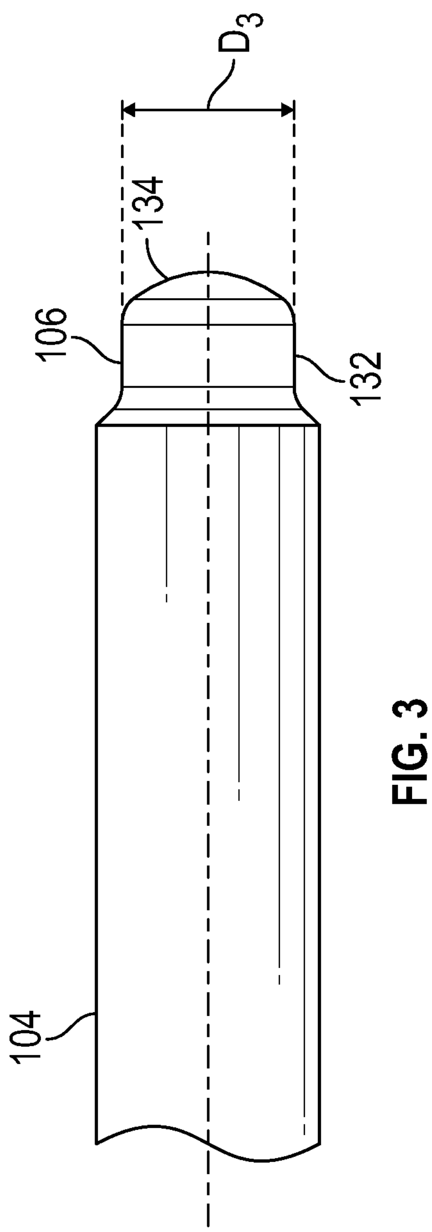
FIG. 3 is a diagram of an outer profile of a tip portion of the orthopedic bone screw of FIG. 1.

FIGS. 1-3 illustrates an example of an orthopedic bone screw 100. The bone screw 100 includes a head 102 and a shaft 104 (also referred to as a shank) extending from the head 102. The shaft 104 includes a threadless atraumatic tip 106. The bone screw 100 can define a longitudinal axis 105. For purposes of this description, the direction toward the head 102 of the screw is referred to as the proximal direction and the direction toward the threadless atraumatic tip 106 is referred to as the distal direction.

In the illustrated example, the shaft 104 can comprise a plurality of threads 110. The illustrated bone screw is configured as a cortical bone screw in which the threads 110 of the shaft 104 are configured to engage cortical bone tissue. However, it should be understood that the various features described herein can be applicable to any type of orthopedic screw, including locking cortical bone screws (e.g., screws comprising threads on the head), locking and non-locking cancellous bone screws, etc.

Figure 4:
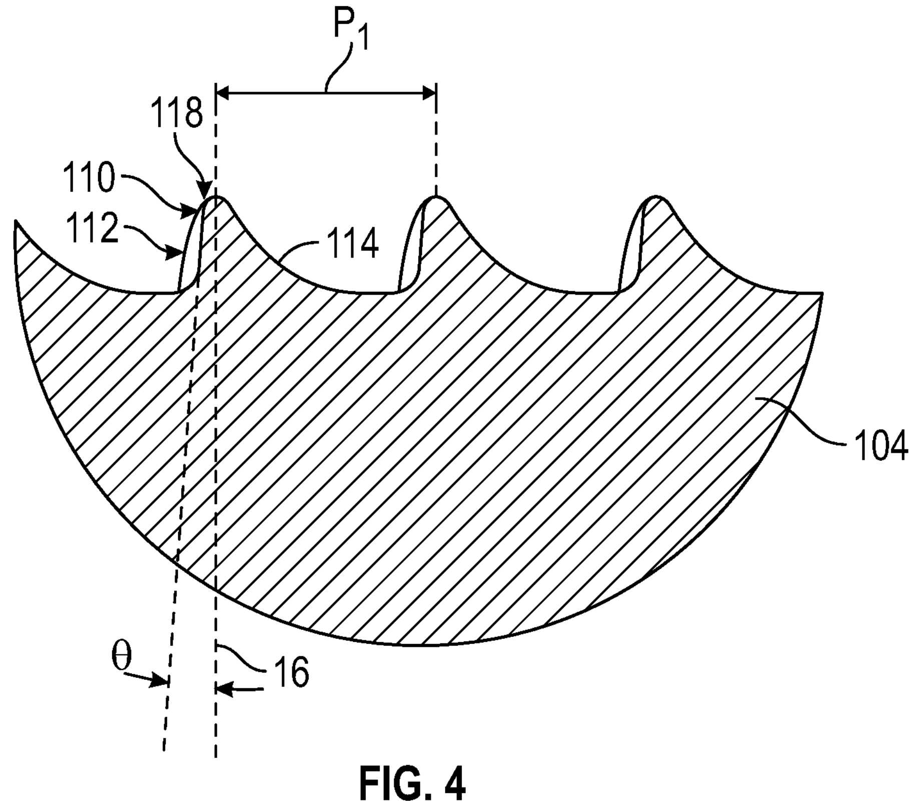
FIG. 4 is a cross-sectional view of a section of the threads of the orthopedic bone screw of FIG. 1.

In certain examples, the threads 110 of the shaft 104 can be single-lead threads. Referring to FIG. 4, in certain examples the threads 110 can be buttress threads having a square or flat first face 112 (e.g., oriented proximally toward the head 102) and an angled and/or curved second face 114 (e.g., oriented distally toward the atraumatic tip 106). In the illustrated example, the first faces 112 of the threads 110 can define an angle θ with a reference axis 116 that is perpendicular to the longitudinal axis 105 of the bone screw. In certain examples, the angle θ can be 0° to 10°, such as 1° to 7° or 5°. The apices 118 of the threads 110 can also be rounded, as in the illustrated example, or pointed. As indicated in FIG. 4, the threads 110 can have a thread pitch $P_1$. Buttress threads can increase the "pushout force" of the bone screw, which is the force needed push or pull the bone screw out of a bone into which it has been threaded. In some examples, the thread pitch $P_1$ of any of the examples herein can be 0.5 mm to 1.2 mm, such as 0.5 mm to 1 mm or 0.8 mm.

Figure 6:
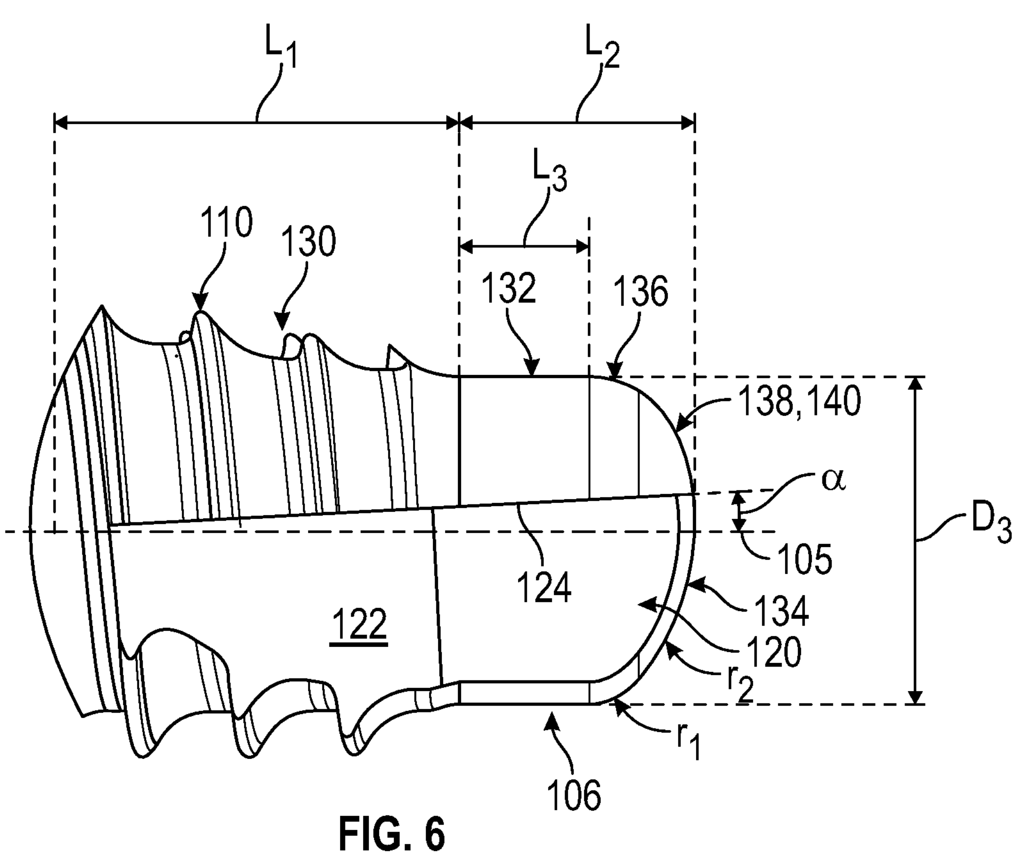

Referring again to FIGS. 2 and 3, the threads 110 can have a major diameter indicated at $D_1$ and a minor diameter indicated at $D_2$. As best shown in FIGS. 2 and 6, the shaft 104 can comprise a thread runout region 130 (also referred to as a transition region) in which the thread height of the threads 110 gradually increases moving in the proximal direction from the atraumatic tip 106. As shown in FIG. 6, in certain examples the thread runout region 130 can comprise a length $L_1$. In certain examples, the thread runout region 130 can comprise one thread or a plurality of threads (e.g., the runout region can include one or a plurality of revolutions of the threads about the circumference of the shaft), such as two threads, three threads, four threads, five threads, etc. In the illustrated embodiment the thread runout region 130 comprises four threads 110.

Figure 5:
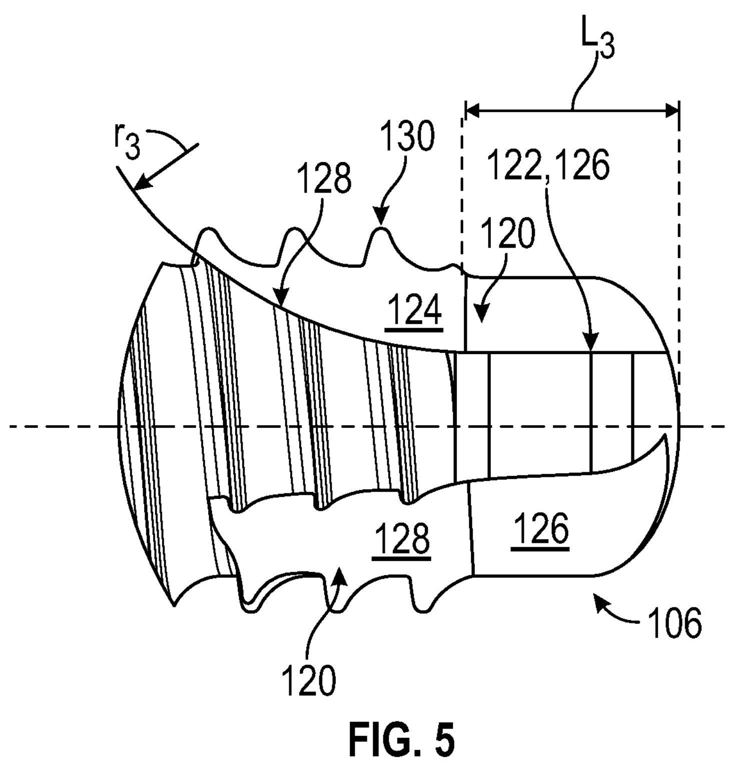

Referring to FIGS. 5 and 6, in the illustrated example the bone screw 100 is configured as a self-tapping bone screw and comprises a plurality of cutting flutes 120 formed in the distal end portion of the bone screw. Each of the cutting flutes 120 can comprise a first radially extending surface 122 and a second radially extending surface 124. The first radially extending surfaces 122 can comprise flat first portions 126 and curved second portions 128 proximal of the first portions 126. In certain examples, the curved second portions 128 can have a radius $r_3$ as indicated in FIG. 5.

Referring again to FIG. 6, the second radially extending surfaces 124 can be flat and/or planar, and can define an angle α with the longitudinal axis 105 of the bone screw. In certain examples, the angle α can be 1° to 10°, such as 1° to 5°. In one particular example, the angle α can be 3°.

The cutting flutes 120 can extend along all or a portion of the threadless atraumatic tip 106. For example, in the illustrated embodiment the cutting flutes 120 can begin on the spherical end surface 140 of the threadless atraumatic tip 106 and can extend proximally along the threadless atraumatic tip 106 and into the thread runout region 130.

Figure 7:
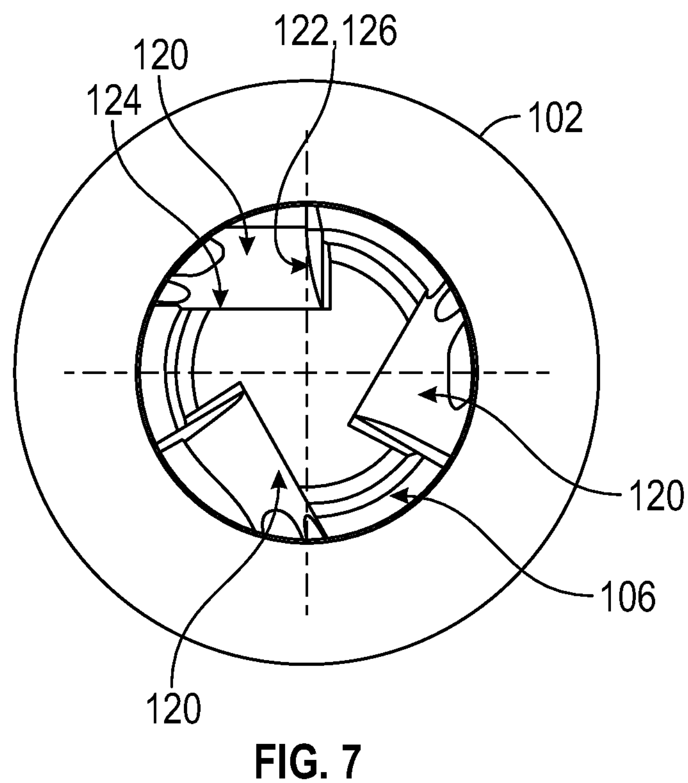
FIG. 7 is a tip end view of the orthopedic bone screw of FIG. 1.

Referring to FIG. 7, the bone screw 100 comprises three self-tapping flutes 120 angularly spaced by 120°, although the bone screw can have more or fewer flutes at any selected angular spacing. The first and second surfaces 122, 124 of each flute 120 can define an angle of 90° with each other, although other configurations are possible. Providing three or more flutes 120 can reduce the torque needed to initiate threading of the bone screw into both cancellous and cortical bone as compared to existing bone screws.

Referring again to FIGS. 5 and 6, the threadless atraumatic tip 106 can be formed as a threadless (e.g., thread free) portion of the shaft 104 at the distal end of the bone screw, and can also be referred to as an atraumatic pilot point or an atraumatic dog point. Referring to FIG. 6, the threadless atraumatic tip 106 can comprise a cylindrical portion 132 and a rounded end portion 134. The overall length $L_2$ of the threadless atraumatic tip 106 including the cylindrical portion 132 and the rounded end portion 134 is indicated in FIG. 6. The cylindrical portion 132 can have a diameter $D_3$ (FIG. 3). In certain examples, the length $L_2$ of the threadless atraumatic tip can be 50% to 150% of the diameter $D_3$ of the cylindrical portion 132, such as 50% to 100% of the diameter $D_3$, 50% to 80% of the diameter $D_3$, 60% to 80% of the diameter $D_3$, 70% to 80% of the diameter $D_3$, 60% to 100% of the diameter $D_3$, 70% to 150% of the diameter $D_3$, 70% to 100% of the diameter $D_3$, etc. In a particular embodiment the length $L_2$ of the threadless atraumatic tip can be 75% of the diameter $D_3$ of the cylindrical portion 132.

Referring to FIG. 6, the cylindrical portion 132 of the threadless atraumatic tip can have a length $L_3$. In certain examples, the length $L_3$ of the cylindrical portion 132 can be proportional to the major diameter $D_1$ of the threads 110. For example, in certain examples the length $L_3$ of the cylindrical portion 132 can be 10% to 150% of the major diameter $D_1$ of the threads 110, such as 10% to 100%, 10% to 80%, 10% to 60%, 10% to 40%, 20% to 150%, 20% to 100%, 20% to 80%, 20% to 60%, 20% to 40%, 25% to 150%, 25% to 100%, 25% to 80%, 25% to 60%, 25% to 40%, etc., of the major diameter $D_1$ of the threads 110. In the illustrated example, the length $L_3$ of the cylindrical portion 132 is 40% of the major diameter $D_1$ of the threads 110. As described in greater detail below, sizing the cylindrical portion 132 within the ranges above facilitates aligning the orthopedic bone screw with the axis of a pre-drilled hole in a bone when the cylindrical portion 132 is inserted into the pre-drilled hole. This configuration can also result in each of the cutting flutes 120 being positioned in contact and aligned with the walls of the pre-drilled hole before driving the screw, which can significantly reduce the compressive force required to initiate threading of the orthopedic bone screw into the bone.

Referring again to FIG. 6, in certain examples the rounded end portion 134 can comprise a plurality of portions having different radii. For example, in the illustrated configuration the rounded end portion 134 comprises a first curved portion 136 and a second curved portion 138 that defines an end surface 140 of the threadless atraumatic tip 106. The first curved portion 136 can have a first radius $r_1$, and the second curved portion can have a second radius $r_2$ that is different from the first radius $r_1$. In certain examples, the second radius $r_2$ of the second curved portion 138 (and thus of the end surface 140) is greater than the first radius $r_1$ of the first curved portion 136. In certain examples, the first radius $r_1$ can be 10% to 90% of the second radius $r_2$, such as 10% to 75%, 10% to 50%, 10% to 40%, 20% to 50%, 20% to 40%, or 20% to 30% of the second radius $r_2$. Thus, in certain examples the first curved portion 136 can be configured as a fillet surface portion or transition surface between the cylindrical portion 132 and the end surface 140 of the threadless atraumatic tip 106 to avoid a ridge or sharp transition between the surfaces.

In certain examples, the diameter $D_3$ of the cylindrical portion 132 can be within a range of ±10% of the minor diameter $D_2$ of the threads 110, such as ±5%, ±4%, ±3%, etc., of the minor diameter $D_2$ of the threads 110 (FIG. 2). In certain examples, the diameter $D_3$ of the cylindrical portion 132 can be substantially equal to the minor diameter $D_2$ of the threads 110. In certain examples, the diameter $D_3$ of the cylindrical portion 132 can be 90% to 100% of the minor diameter $D_2$ of the threads 110, such as 95% to 100% of the minor diameter $D_2$ of the threads 110.

In certain examples, the length $L_3$ of the cylindrical portion 132 of the threadless atraumatic tip 106 can be 100% to 500% of the thread pitch $P_1$ of the threads 110, such as 100% to 400%, 100% to 300%, 100% to 200%, etc. In a particular example, the length $L_3$ of the cylindrical portion 132 can be 175% of the thread pitch $P_1$ of the threads 110.

In certain examples, the length $L_3$ of the cylindrical portion 132 of the threadless atraumatic tip 106 can be 10% to 200% of the diameter $D_3$ of the cylindrical portion 132, such as 25% to 200%, 25% to 100%, 25% to 75%, etc. In a particular example, the length $L_3$ of the cylindrical portion 132 can be 50% of the diameter $D_3$ of the cylindrical portion 132.

In certain examples, the overall length $L_2$ of the threadless atraumatic tip 106 (e.g., the length $L_3$ of the cylindrical portion 132 plus the axial length of the round end portion 134) can be 100% to 600% of the thread pitch $P_1$ of the threads 110, such as 100% to 500%, 100% to 400%, 100% to 300%, 200% to 600%, 200% to 500%, 200% to 400%, 200% to 300%, etc. In a particular example, the overall length $L_2$ of the threadless atraumatic tip 106 can be 250% of the thread pitch $P_1$ of the threads 110.

Figure 8:
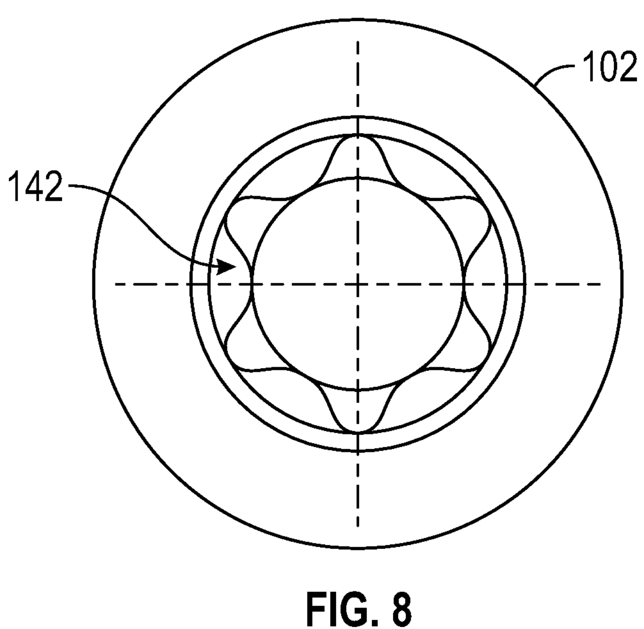
FIG. 8 is a head end view of the orthopedic bone screw of FIG. 1.

Referring to FIG. 8, in the illustrated example the head 102 can define a drive socket 142. In certain examples, the drive socket 142 can be configured to receive a multi-lobed driver bit (e.g., coupled to a powered driver such as a drill). In the illustrated example, the drive socket includes six angularly spaced recesses configured to receive a hexalobular driver bit. However, the drive socket 142 can be configured to receive a driver bit having any configuration (e.g., a hexagonal driver bit, a Philips driver bit, etc.).

Figure 9:
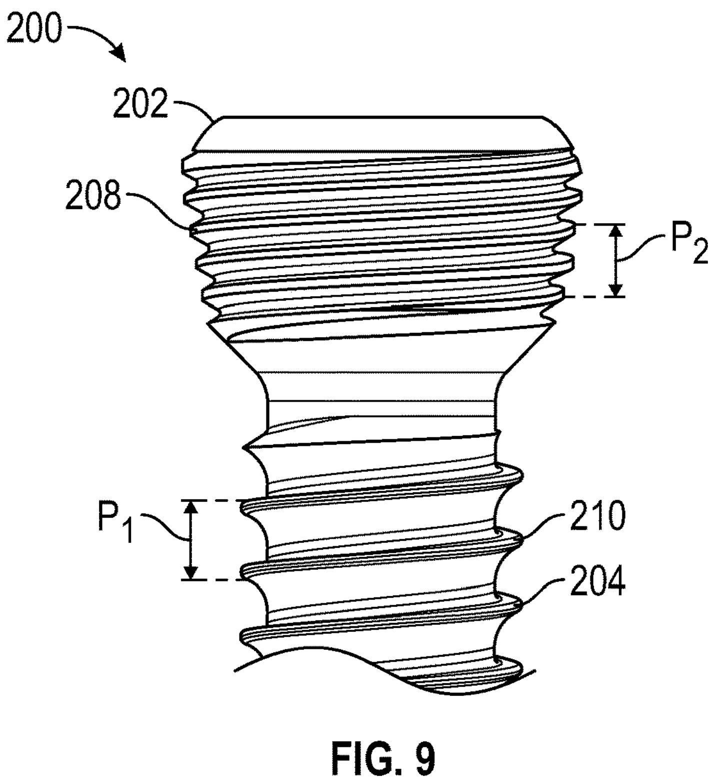
FIG. 9 is an elevational view of the head portion and a portion of the shaft of a locking bone screw according to another example.

In certain examples, the features described herein such as the threadless atraumatic tip can be applicable to locking cortical screws including threads on the head for engaging internal threads in the hole of a bone plate or other orthopedic fixation. FIG. 9 illustrates a representative example of a locking cortical screw 200 including a shaft 204 having first threads 210 and a head 202 including second threads 208. In certain examples, the second threads 208 of the head 202 can be multiple-lead threads. For example, in the illustrated configuration the second threads 208 are configured as double-lead threads (also referred to as "two-lead" and "double start" threads). In certain examples, the double-lead second threads 208 comprise two thread grooves initiated 180° apart on the circumference of the proximal and distal ends of the head 202. In other embodiments, the second threads can be single-lead threads, triple-lead threads, etc., depending upon the particular characteristics sought.

In certain examples, the first threads 210 of the shaft 204 can have a first thread pitch $P_1$ and the second threads 208 of the head can have a second thread pitch $P_2$. In certain examples, the thread pitch $P_1$ of the first threads 210 can be different from the pitch $P_2$ of the second threads 208. For example, in certain examples the thread pitch $P_2$ of the second threads 208 on the head 202 can be greater than the pitch $P_1$ of the first threads 210 on the shaft 204. The result of this configuration is that when the bone screw 200 is driven into a bone through a bone plate or other fixation having a threaded screw hole and the second threads 208 of the head 202 engage the threads of the bone plate, the head 202 can travel a greater linear distance than the shaft 204 per revolution of the bone screw. This can have the effect of moving or "lifting" the bone plate away from the surface of the bone as the screw is tightened, reducing the compressive load and/or the pressure applied to the bone surface beneath. This can reduce the associated risk of necrosis of the periosteum. In some examples the double lead thread pitch $P_2$ of any of the examples herein can be 0.5 mm to 1.2 mm, such as 0.5 mm to 1 mm or 0.8 mm.

Orthopedic bone screws such as the examples described herein can be manufactured from any of a variety of biocompatible metal materials such as stainless steel (e.g., SAE Type 316LS stainless steel), titanium alloys, cobalt chromium alloys, magnesium alloys, and/or tantalum alloys, any of various polymeric materials including resorbable polymers such as polylactides including poly-L-lactic acid (PLLA), etc.

Figure 10:
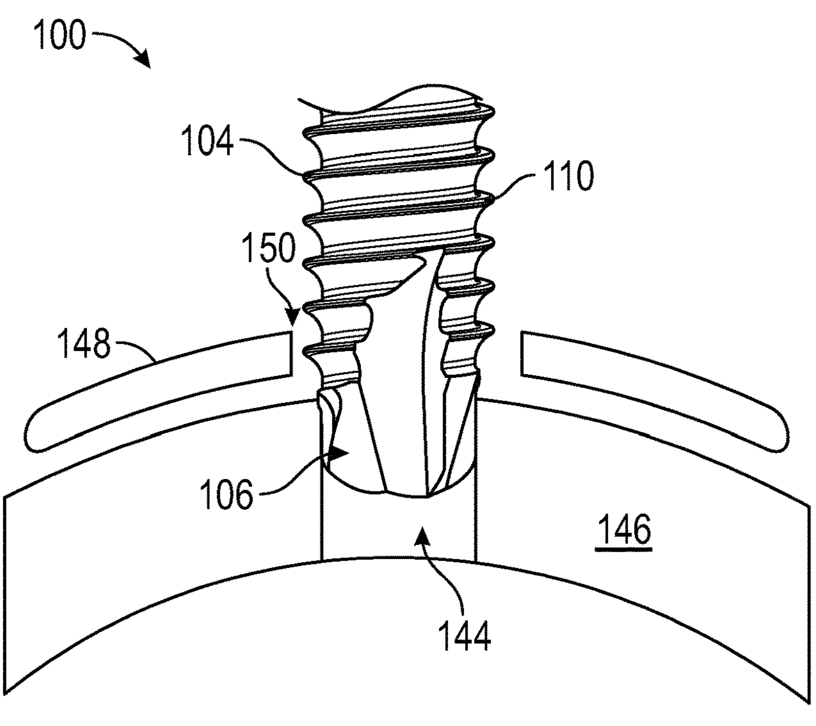
FIG. 10 is a schematic diagram illustrating the tip portion of the orthopedic bone screw of FIG. 1 positioned through a bone plate into a pre-drilled hole in a bone.

In use, the bone screw 100 can be used to secure two or more bone segments/fragments together, and/or to secure a bone plate or other orthopedic fixation device to a bone. For example, with reference to FIG. 10 a hole 144 can be drilled into a bone 146 at a selected position and angle. The diameter of the pre-drilled hole can be selected based on the major diameter of the threads of the orthopedic bone screw to be used. If use of a bone plate is indicated, a bone plate 148 can be positioned over the bone 146 such that a selected screw hole opening 150 in the bone plate 148 overlies and is aligned with the pre-drilled hole 144 in the bone 146. The bone screw 100 can be inserted into the screw hole opening 150 of the bone plate 148 and driven into the pre-drilled hole 144 in the bone. The threadless atraumatic tip 106 can be received in the pre-drilled hole. In examples in which the bone screw is configured as a self-tapping bone screw, the self-tapping flutes 120 at the distal end of the shaft 104 can cut threads into the bone tissue as the screw is driven into the bone. For bone screws configured as locking screws, the threads of the head can engage with corresponding internal threads of the screw hole opening 150 in the bone plate 148 upon final tightening to secure the bone screw 100 to the bone plate 148.

Figure 11:
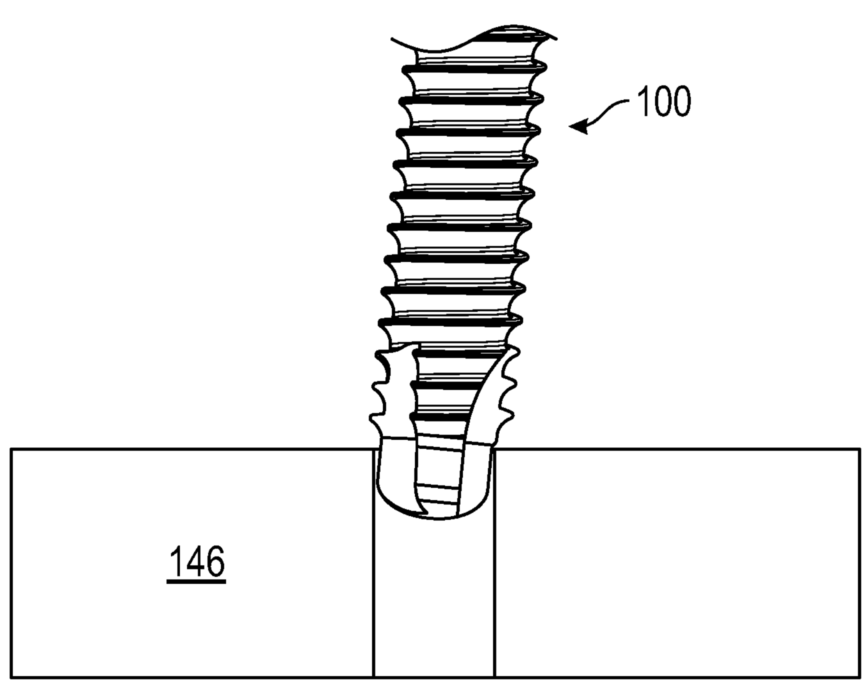
FIG. 11 is a diagram illustrating angulation of an orthopedic bone screw in a hole drilled in a bone.

The bone screw examples and the various features described herein can provide a number of significant advantages over existing bone screws both alone and in various combinations. For example, the threadless atraumatic tip 106 can facilitate accurate alignment of the screw with a pre-drilled hole in a bone. As shown in FIG. 11, the diameter of the pre-drilled hole can be selected by the surgeon based on the diameter of the bone screw to be used. The diameter of the pre-drilled hole can be the same or slightly larger than the diameter $D_3$ of the threadless atraumatic tip. Accordingly, when the bone screw is inserted into the pre-drilled hole, the threadless atraumatic tip can be guided by the walls of the pre-drilled hole. Thus, a bone screw with a threadless atraumatic tip, and particularly a cylindrical portion of the threadless atraumatic tip having the length to thread major diameter relationships described herein can facilitate alignment of the bone screw with the pre-drilled hole. In particular, the inventors have discovered that a threadless atraumatic tip with a cylindrical portion having a length as described herein can limit angulation of the bone screw relative to the pre-drilled hole to within a specified angular range (e.g., 1° to 20°, such as 1° to 10°), as shown in FIG. 11. This, in combination with the configuration of the cutting flutes and the thread runout region on the distal end of the bone screw, can facilitate a more precise alignment of the cutting flutes with the surface of the bone inside the pre-drilled hole. Each of the cutting flutes can also be in contact with the bone before drilling is initiated by virtue of the geometry of the threadless atraumatic tip. The result is a surprising reduction in the axial compression load (force) that is required to engage the self-tapping flutes with the bone material when the screw is driven into the bone. In an exemplary test, the inventors determined that the axial compression load for bone screws configured as described herein was reduced by more than 50% from 8.1 N to 3.5 N as compared to existing bone screws without the threadless atraumatic tip. When combined with the relatively large number of threads and the gradual increase in height of the threads in the runout region, significant reductions in the torque required to advance the bone screw into the bone can also be achieved.

Figure 12:
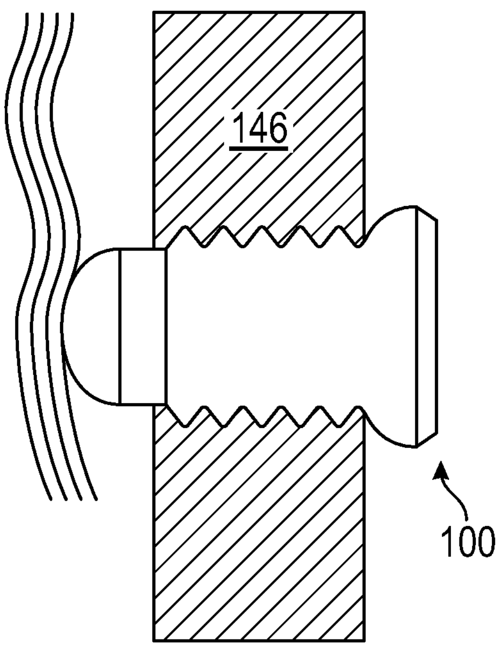
FIG. 12 is a schematic diagram of an orthopedic bone screw inserted through a bone with the atraumatic tip in contact with soft tissue.
Figure 13:
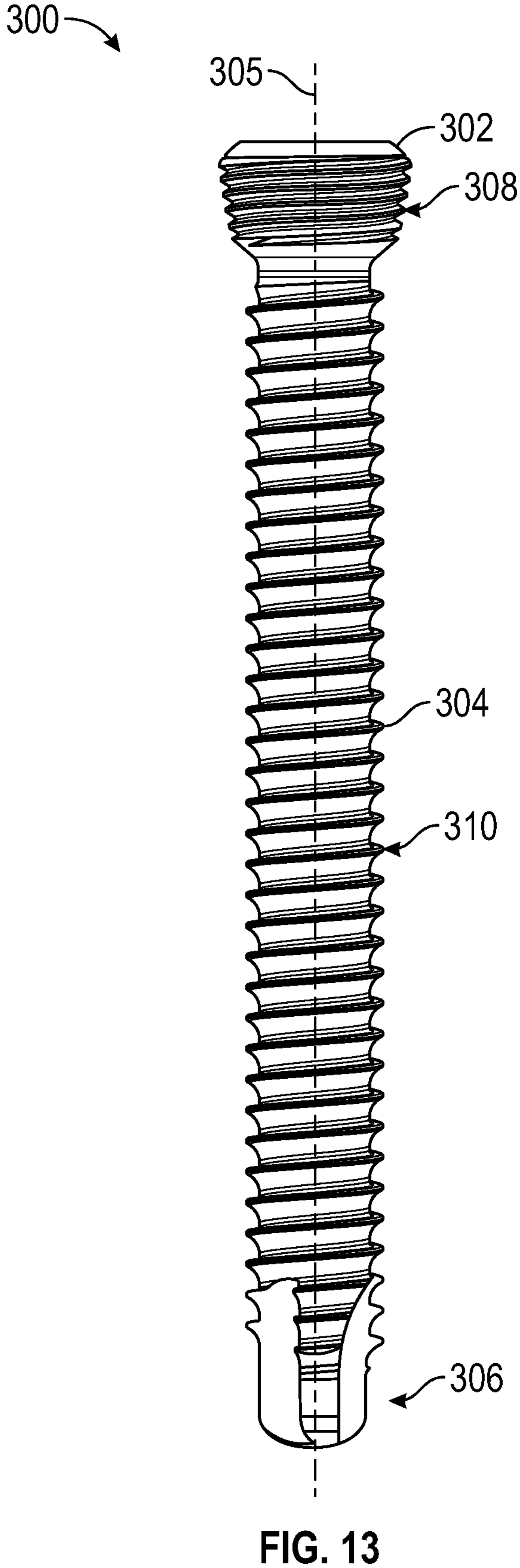
FIG. 13 is a side elevation view of another example of an orthopedic bone screw.

Referring to FIG. 12, in certain orthopedic procedures bone screws can extend through a bone and out the opposite side by a selected length. In such procedures, the smooth, rounded end surface of the threadless atraumatic tip can advantageously reduce irritation of the surrounding soft tissue. Additionally, spacing the runout region axially (e.g., proximally) from the tip of the bone screw by the length of the threadless atraumatic tip (and/or the cylindrical portion) can reduce the likelihood of screw threads protruding from the outlet of the pre-drilled hole on the opposite side of the bone from the head. This can reduce both the length of threads and the thread height profile in contact with soft tissue, providing a further reduction in the potential for soft tissue irritation and related post-operative complications. Stated differently, there are no sharp edges on the bone screw examples described herein that would extend into soft tissue once the screw is driven into a bone.

Additionally, in the case of cortical locking screws, by making the thread pitch $P_2$ of the second threads on the head greater than the thread pitch $P_1$ of the first threads on the shaft, the bone screw can reduce the compressive force applied to the bone by the bone plate when the bone screw is tightened. For example, because the second thread pitch $P_2$ is greater than the first thread pitch $P_1$, when the second threads engage the bone plate the head travels a greater distance than the shaft per revolution of the bone screw. This can have the effect of lifting the bone plate away from the bone as the bone screw is tightened. Lifting the bone plate away from the surface of the bone relieves compressive forces on the periosteum, which can reduce pressure-related necrosis as described above. The resulting structure can also facilitate a strong, independent coupling between the bone screw and the bone plate (e.g., via the second threads of the head) and the bone screw and the bone (e.g., via the first threads of the shaft).

Example 2: Orthopedic Bone Screw with Thread Minor Diameter Transition

FIGS. 13-18 illustrate another example of an orthopedic bone screw 300. The bone screw 300 can be configured similarly to the bone screws 100 and 200, and in FIGS. 13-18 similar reference numbers indicate similar features to those shown in the earlier examples. For example, the bone screw 300 can include a head 302, a shaft 304, and an atraumatic tip portion 306. The shaft 304 can comprise a first thread 310 similar to the other first threads described above. The head 302 can comprise a second thread 308 similar to the second thread 208. For example, the second thread 308 can be multiple lead thread, such as a double-lead thread. The threadless atraumatic tip portion 306 can comprise a cylindrical portion 332, and a rounded end portion including a first curved portion 336 and a second curved portion 338 that defines an end surface 340 of the threadless atraumatic tip 306 similar to the examples described above.

Figure 14:
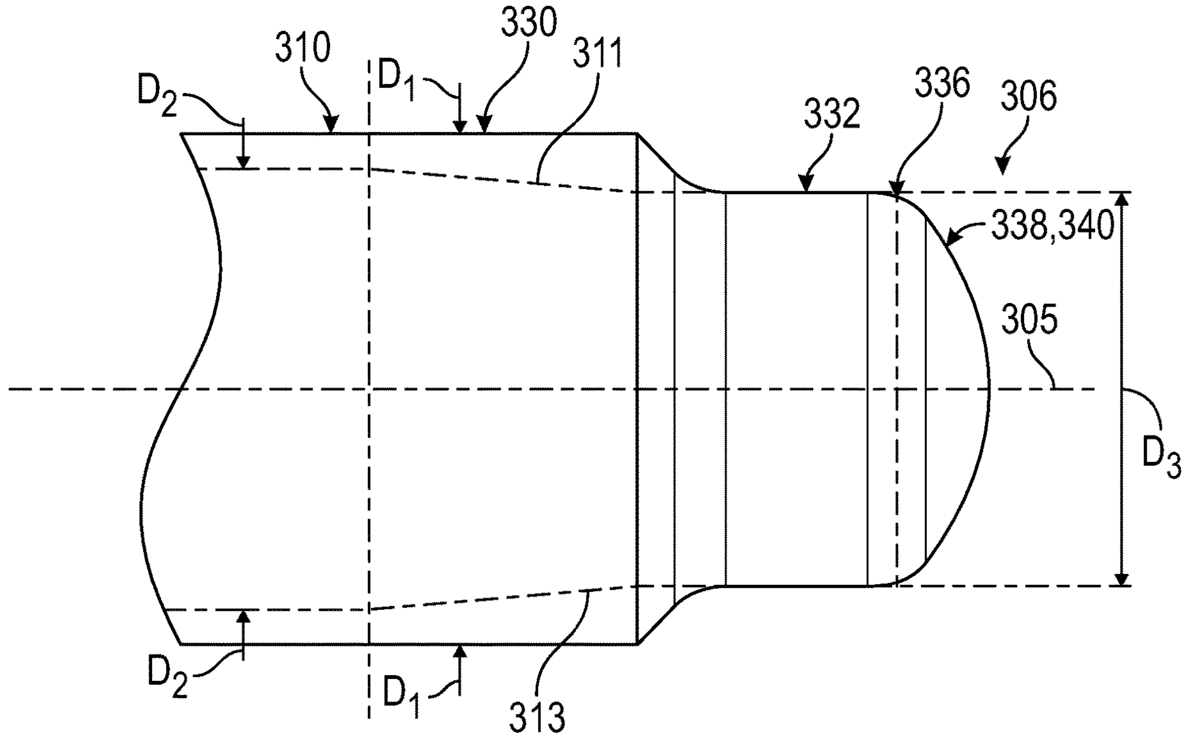
FIG. 14 is a diagram of an outer profile of a tip portion of the orthopedic bone screw of FIG. 13.
Figure 15:
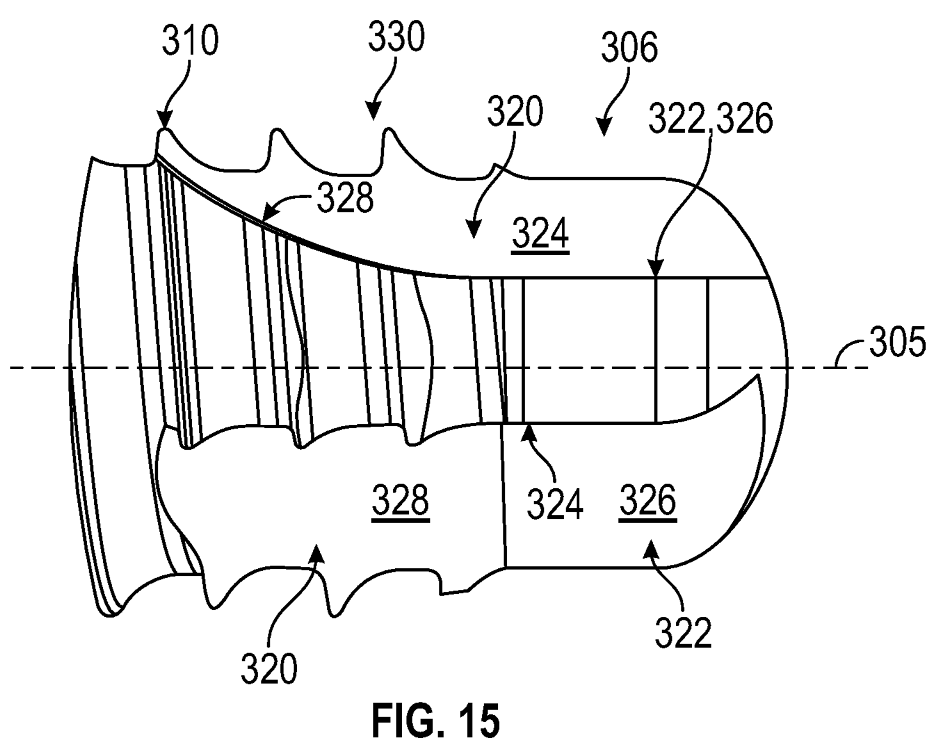

Referring to FIGS. 14 and 15, in certain examples the diameter $D_3$ of the cylindrical portion 332 of the threadless atraumatic tip portion 306 can be slightly smaller than the minor diameter $D_2$ of the first threads 310 as noted above. In some examples, a surgeon can drill a pilot hole in a bone that has a diameter that is equal or substantially equal to the diameter $D_3$ of the cylindrical portion 332 to limit angulation of the bone screw and ensure that the self-tapping threads engage the walls of the hole. Thus, in some examples it can be advantageous to gradually increase the minor diameter of the first threads 310 in the thread runout region 330. For example, FIG. 14 schematically illustrates the minor diameter of the first threads 310 indicated by lines 311 and 313. The lines 311 and 313 are shown diverging in the thread runout region 330 as the minor diameter increases from the diameter $D_3$ of the cylindrical portion 332 to the nominal/specified minor diameter $D_2$. This can prevent a stepwise increase in the diameter of the shaft in cases where the diameter $D_3$ of the cylindrical portion 332 is less than the specified minor diameter $D_2$ of the first threads 310, which can reduce the torque required to initiate threading and drive the screw into the bone. This can also facilitate use of threads having a minor diameter that is greater than the diameter of the atraumatic tip portion, which can improve the axial strength of the bone screw. In certain examples, the minor diameter $D_2$ of the first threads 310 can be 1% to 10% greater than the diameter $D_3$ of the cylindrical portion 332, such as 1% to 8%, 1% to 5%, etc. In a particular example, the diameter $D_3$ of the cylindrical portion 332 can be 2.8 mm and the specified minor diameter $D_2$ of the first threads 310 can be 2.9 mm such that gradually increasing the minor diameter of the threads eliminates a 0.1 mm step in the thread runout region 330. The transition of the thread minor diameter from the diameter $D_3$ of the cylindrical portion 332 to the specified minor diameter $D_2$ can occur over the entire length of the thread runout region 330, or a portion thereof. The rate of increase of the thread minor diameter can be constant along the length of the thread runout region 330 as shown in FIG. 14, or non-constant such as exponential.

Figure 16:
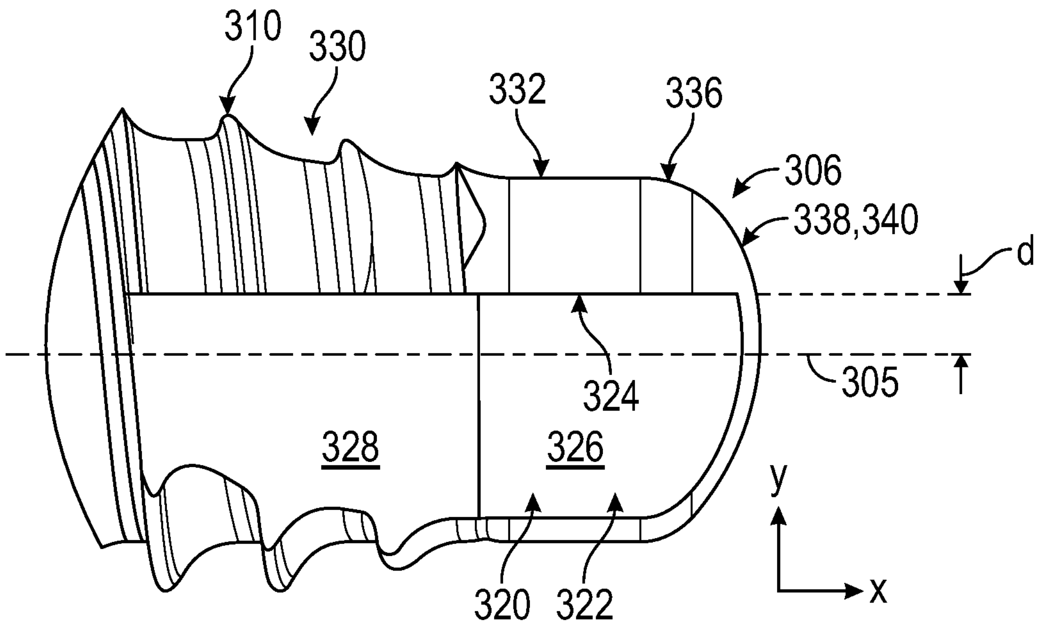

Referring to FIGS. 15 and 16, the cutting flutes 320 can comprise first radially extending surfaces 322 and second radially extending surfaces 324. The first radially extending surfaces 322 can comprise flat first portions 326 and curved second portions 328 proximal of the first portions 326 similar to the examples above. The flat first portions 326 (also referred to as "flat surface portions") can be in the threadless atraumatic tip 306 (e.g., coextensive with the threadless atraumatic tip 306). The curved second portions 328 (also referred to as "curved surface portions") can be in the thread runout region 330 (e.g., coextensive with the thread runout region 330).

Figure 17:
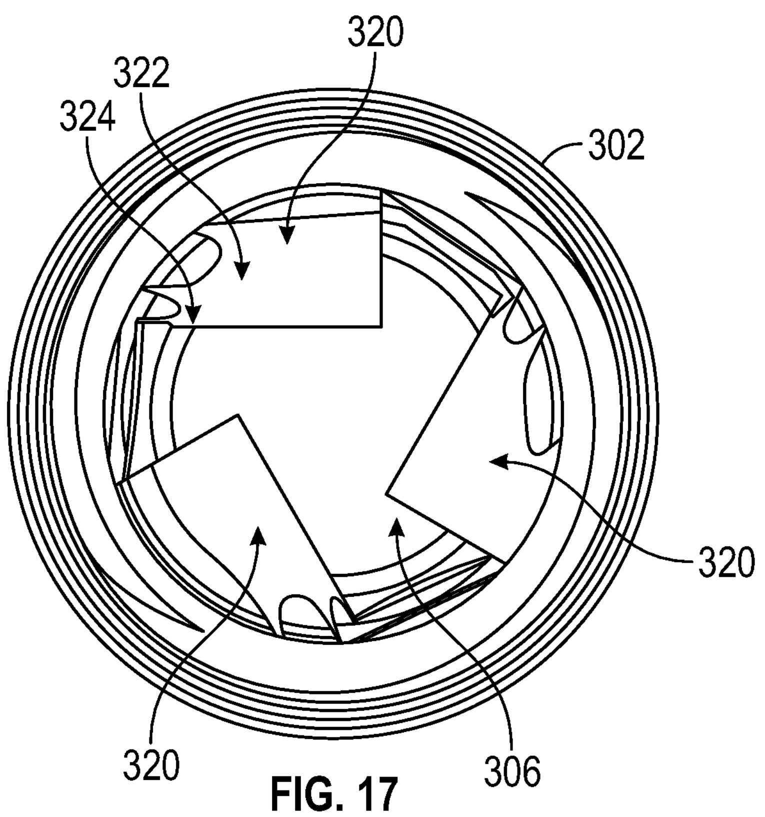
FIG. 17 is a tip end view of the orthopedic bone screw of FIG. 13.

In some examples the second radially extending surface 324 of each cutting flute 320 can be parallel or substantially parallel to the longitudinal axis 305. Stated differently, the surface 324 can be flat and parallel to the longitudinal axis 305 in the atraumatic tip portion and in the thread runout region. This can increase the cutting angle of the self-tapping threads (e.g., in the thread runout region 330), which can improve the initiation of threading when driving the bone screw into a bone. Additionally, the second radially extending surfaces 324 can also be offset from the longitudinal axis 305 when viewed edge-on. For example, as shown in FIG. 16, when the perspective of the viewer is aligned with the longitudinal edge of one of the second radially extending surfaces 324, the second radially extending surface 324 can be offset from the longitudinal axis 305 along the positive y-axis in FIG. 16 by a distance d. In some examples, the offset distance d can be a radial offset relative to the longitudinal axis 305. In certain examples, the distance d can be 5% to 25% of the diameter $D_3$ of the cylindrical portion 332, such as 5% to 20%, 5% to 15%, 10% to 25%, 10% to 15%, etc. An end view of the bone screw 300 illustrating the cutting flutes 320 is shown in FIG. 17.

Figure 18:
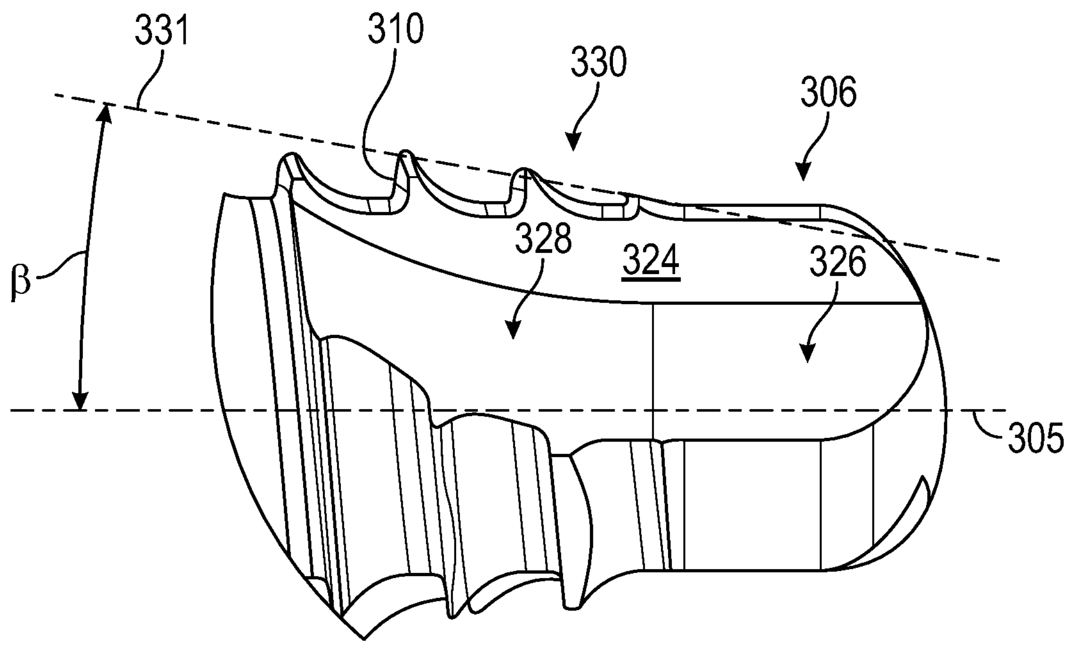
FIG. 18 is a side elevation view of the tip portion of the orthopedic bone screw of FIG. 13 illustrating an angle formed by apices of the threads in the thread runout region.

In certain examples, the apices of the threads can define an angle with the longitudinal axis of the bone screw as the thread height increases in the thread runout region 330. Stated differently, the threads can increase in height in the thread runout region 330 in such a manner that a line tangent to the peaks of the threads in the thread runout region can define a specified angle. For example, FIG. 18 illustrates three threads 310 in the thread runout region 330 increasing in height in the proximal direction such that a line 331 that is tangent to the peaks of the threads 310 forms an angle β with the longitudinal axis 305. In certain examples, the angle β can be 5° to 30°, such as 5° to 20°, 5° to 15°, or 10°. Increasing the thread height according to the angle ranges recited herein can truncate the height of the leading threads for each cutting flute. This can allow the cutting depth of the threads to ramp up as the screw is driven into the bone, which can reduce the force required during initial threading into the bone and can also reduce the risk of fracture.

Figure 19:
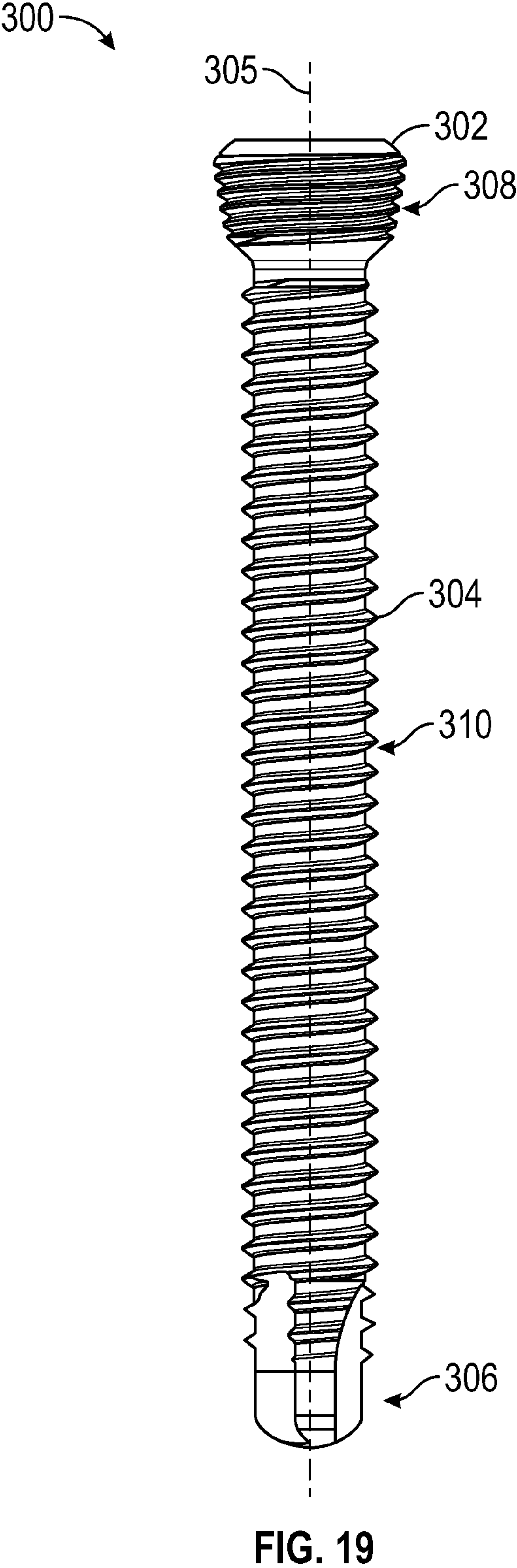
FIG. 19 is a side elevation view of another example of the orthopedic bone screw of FIG. 13 with a shaft including threads having a different thread profile.
Figure 20:
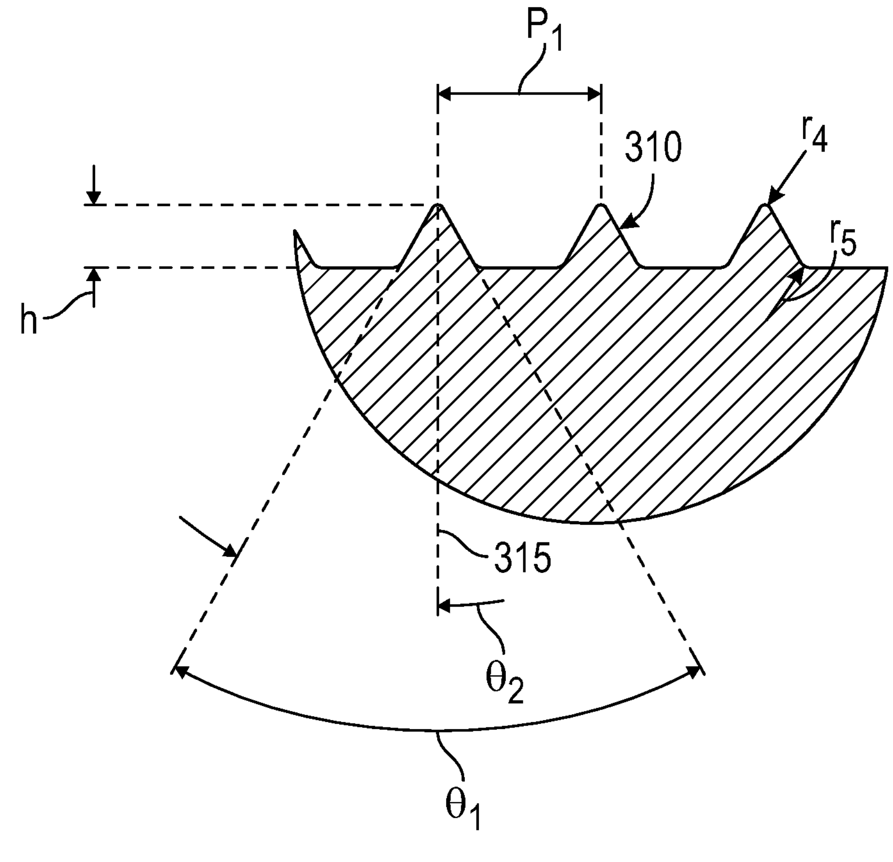
FIG. 20 is a cross-sectional view of a section of the threads of the orthopedic bone screw of FIG. 19.
Figures 21, 22:
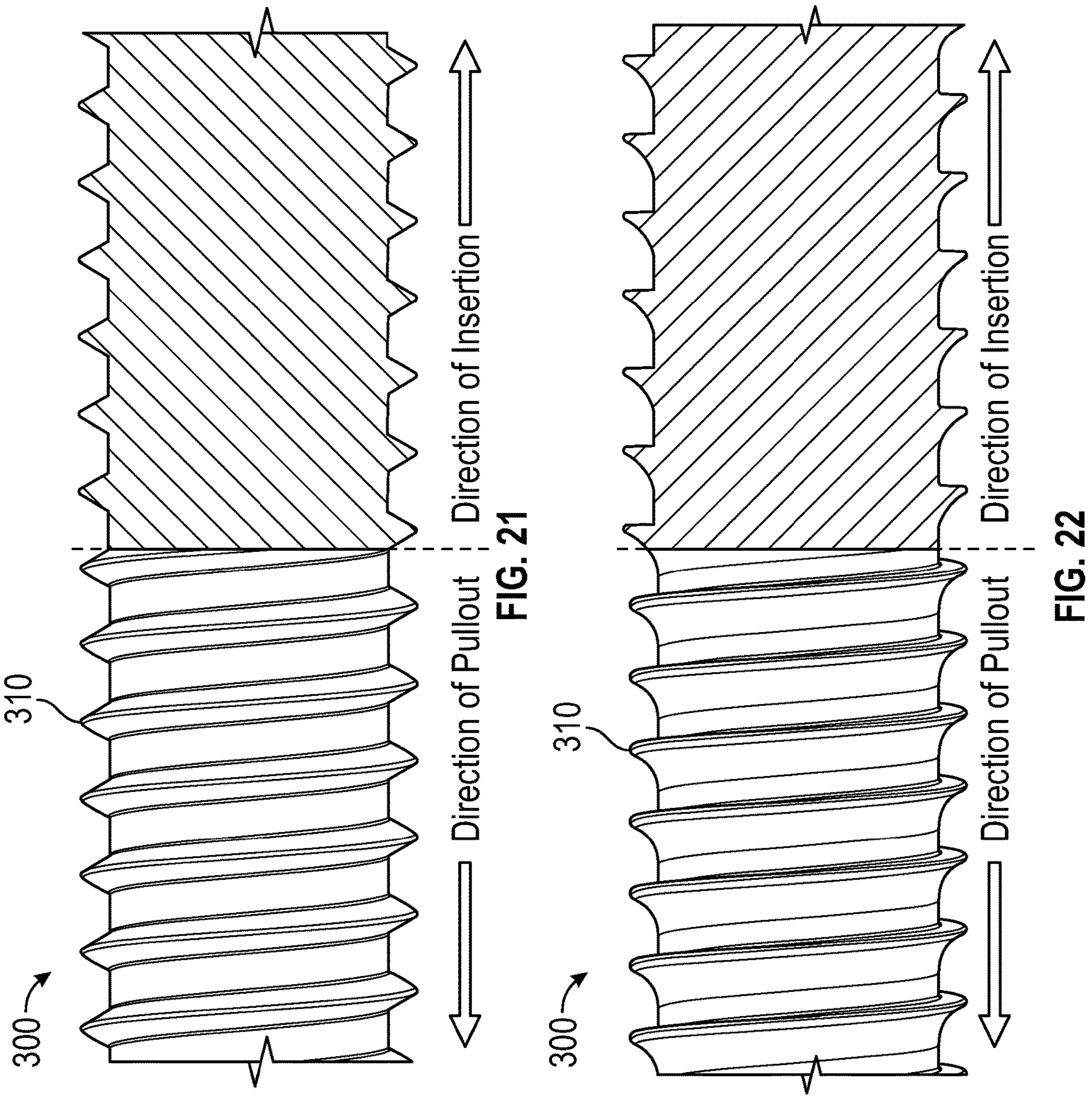
FIG. 21 illustrates a partial cross-sectional view of the bone screw of FIG. 19.
FIG. 22 is a partial cross-sectional view of the bone screw of FIG. 19 including an example of a reverse buttress thread.

Any of the screw examples described herein can also include other thread profiles on the shaft. For example, FIGS. 19-21 illustrate another example of the orthopedic bone screw 300 in which the first threads 310 have symmetric sides that form an angle $\theta_1$. Referring to FIG. 20, the peaks/apices of the threads can have a radius $r_4$ and the roots of the threads can have a radius $r_5$ that is larger than the radius $r_4$. The walls of the threads can define an angle $\theta_2$ with central axes 315 of the threads. In some examples the angle $\theta_2$ can be 0° to 90°, such as 10° to 60°, 10° to 50°, 10° to 40°, 10° to 30°, etc. In some examples, the proximal walls of the screw threads can have an angle $\theta_2$ such that the angle of the proximal walls in the pull out direction (e.g., proximally toward the head) is 10° to 60°, 60° or less, or any of the other angle ranges herein. In some examples the angle $\theta_1$ can be 60° and the angle $\theta_2$ can be 30° as in a metric MJ thread profile. The threads can have a thread height h and a pitch $P_1$. In certain examples the radius $r_4$ can be 4% to 12% of the thread height h, such as 6% to 10% or 8% of the thread height h. In certain examples, the radius $r_5$ can be 10% to 100% of the thread height h, such as 20% to 50% or 33% of the thread height h. Certain examples of orthopedic bones screws with thread profiles as shown in FIGS. 19-21 have exhibited improved pullout strength in tests.

Figures 23, 24:
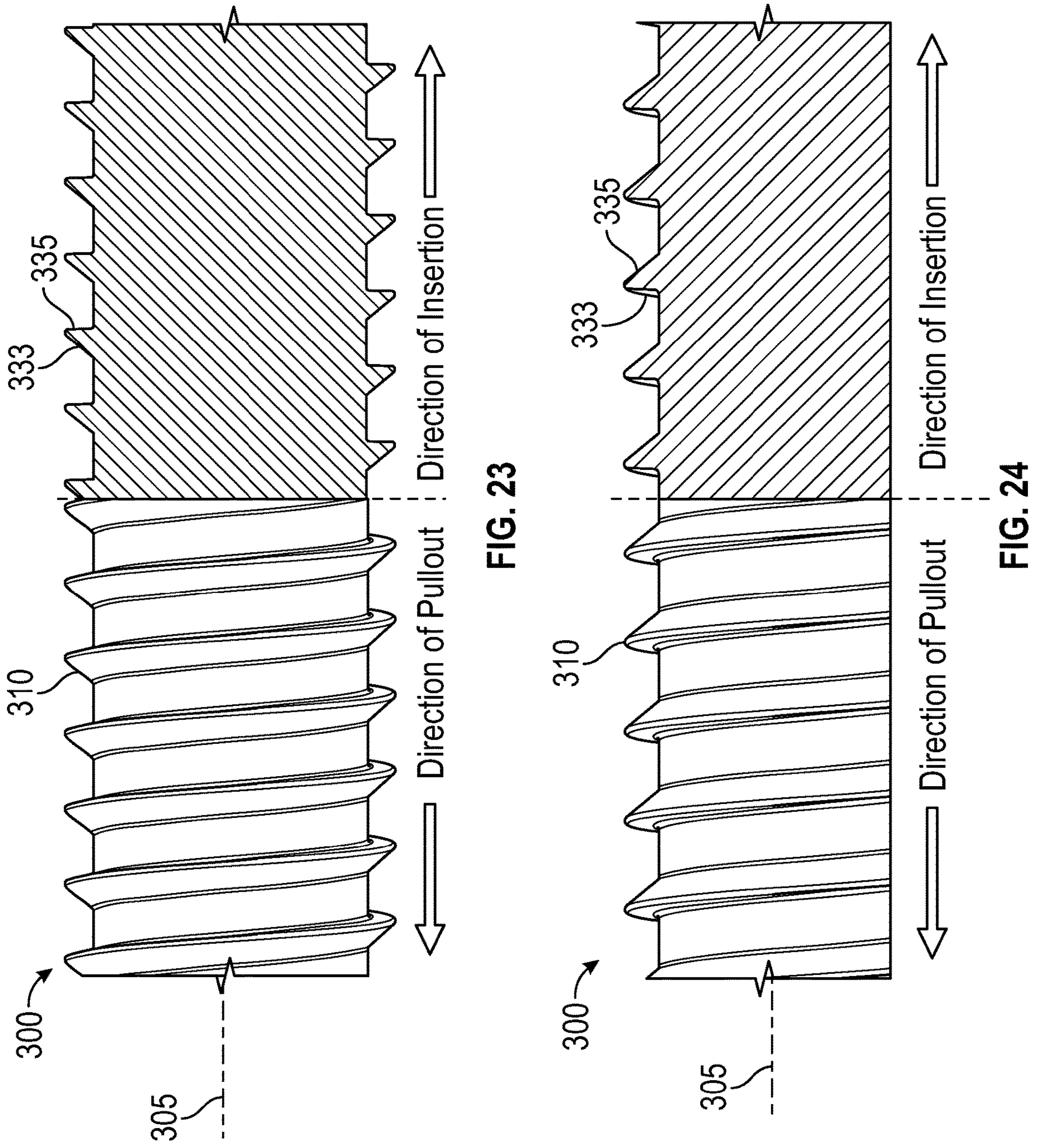
FIG. 23 is a partial cross-sectional view of the bone screw of FIG. 19 including an example of an angled reverse buttress thread.
FIG. 24 is a partial cross-sectional view of the bone screw of FIG. 19 including an example of an angled buttress thread.

In yet other examples, the first threads 310 (or the first threads of any of the other screw examples herein) can be configured as "reverse" buttress threads in which the flat face is oriented distally toward the atraumatic tip and the curved face is oriented proximally toward the head of the screw. An example of the bone screw 300 with first threads 310 configured as reverse buttress threads is shown in FIG. 22. In FIG. 22, the proximal surfaces of the first threads 310 (oriented in the pullout direction toward the head) are curved. In other examples, the proximal and distal surfaces of the buttress threads can both be flat/planar. For example, FIG. 23 illustrates an example of the bone screw 300 in which the first threads 310 have planar proximal surfaces 333 that are angled relative to the longitudinal axis 305 (e.g., by 30° to 70°, 40° to 70°, 45° to 60°, etc.). The first threads 310 can also have planar distal surfaces 335 that are perpendicular or substantially perpendicular to the longitudinal axis 305. The threads 310 can also have rounded (also referred to as a "curved" and "radiused") apices. FIG. 24 illustrates a bone screw 300 in which the first threads 310 are buttress threads having the opposite configuration with the distal surface 335 being angled relative to the longitudinal axis 305 and the proximal surfaces 333 being perpendicular or substantially perpendicular to the longitudinal axis.

Figure 25:
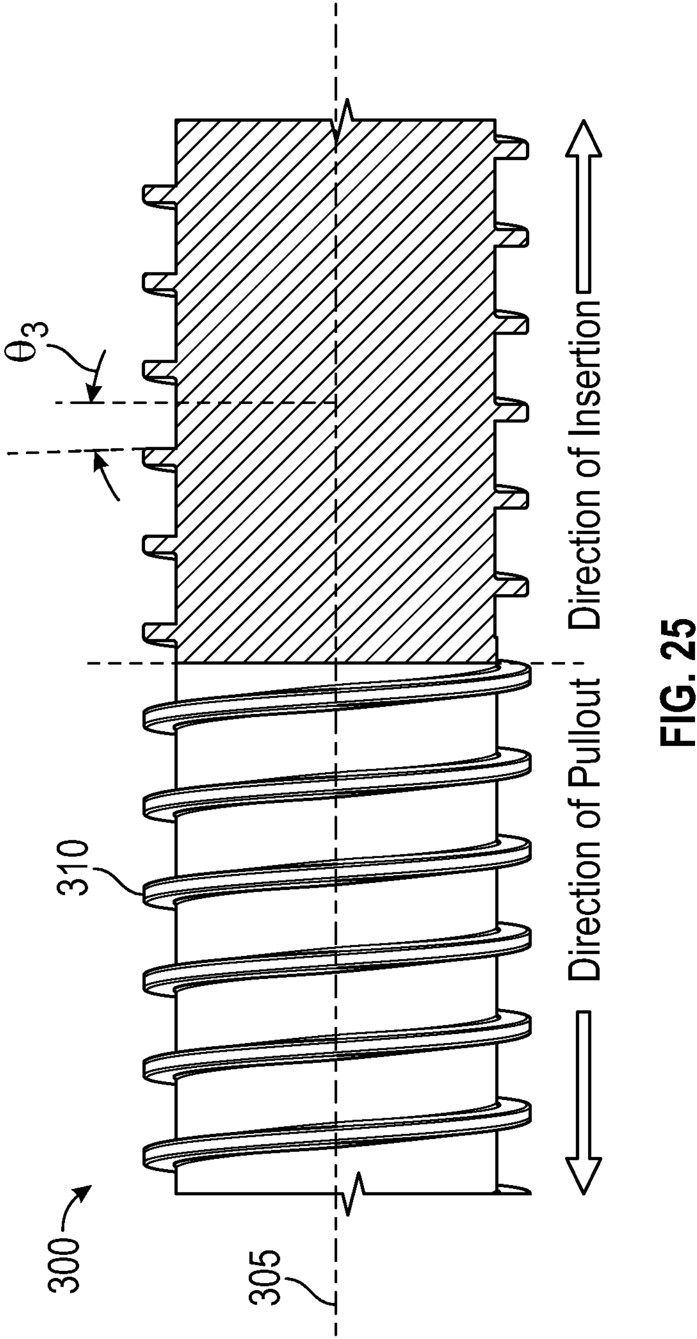
FIG. 25 is a partial cross-sectional view of the bone screw of FIG. 19 including an example of an Acme thread.

FIG. 25 illustrates another thread profile that can be implemented on the first threads of any of the bone screw examples described herein. The walls (also referred to as "flanks") of the first threads 310 can define an angle $\theta_3$ of 1° to 20°, such as 1° to 15°, 1° to 10°, 1° to 5°, 3° to 20°, 3° to 15°, 3° to 10°, or 3° to 5°. In some examples, the first threads 310 in FIG. 25 can be configured as "Acme" threads with an angle between opposing thread flanks of 29°, "trapezoidal" threads with an angle between opposing thread flanks of 30°, or "square" threads with 90° thread flanks measured relative to the longitudinal axis 305 of the shaft. The threads 310 can be radiused at the root where the threads originate from the shaft, and radiused or filleted along the upper surfaces.

Additional Examples of the Disclosed Technology

It should be understood that any of the features of the orthopedic bone screws described herein can be used in various combinations with any of the other orthopedic bone screws described herein. For example, the thread minor diameter transition can be implemented on the bone screw 100 and/or the bone screw 200 as well as the bone screw 300. Additionally, Any of the bone screws 100, 200, and/or 300 can include cutting flutes with flat/planar surfaces that are parallel or substantially parallel to the screw shaft axis and offset from the screw shaft axis when viewed edge-on similar to the surface 324 of the bone screw 300.

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. An orthopedic bone screw comprises a head; and a shaft extending from the head and comprising threads, the threads comprising a major diameter and a minor diameter; the shaft comprising a threadless atraumatic tip opposite the head Example 2. The orthopedic bone screw of any example herein, particularly example 1, wherein the threadless atraumatic tip comprises a cylindrical portion that is distal of the threads, and a round end portion that is distal of the cylindrical portion and forms a tip of the orthopedic bone screw.

Example 3. The orthopedic bone screw of any example herein, particularly example 2, wherein a length of the cylindrical portion of the atraumatic tip is 25% to 150% of the major diameter of the threads.

Example 4. An orthopedic bone screw, comprising: a head; and a shaft extending from the head and comprising threads, the threads comprising a major diameter and a minor diameter; the shaft comprising a threadless atraumatic tip opposite the head, the threadless atraumatic tip comprising a cylindrical portion that is distal of the threads, and a round end portion that is distal of the cylindrical portion and forms a tip of the orthopedic bone screw; wherein a length of the cylindrical portion of the atraumatic tip is 25% to 150% of the major diameter of the threads.

Example 5. The orthopedic bone screw of any example herein, particularly example 4, wherein a diameter of the cylindrical portion of the threadless atraumatic tip is 90% to 100% of the minor diameter of the threads.

Example 6. The orthopedic bone screw of any example herein, particularly example 4 or example 5, wherein an overall length of the threadless atraumatic tip is 50% to 100% of a diameter of the cylindrical portion of the threadless atraumatic tip.

Example 7. The orthopedic bone screw of any example herein, particularly any one of examples 1-6, wherein the threads comprise a thread pitch, and the length of the cylindrical portion of the threadless atraumatic tip is 100% to 500% of the thread pitch.

Example 8. The orthopedic bone screw of any example herein, particularly any one of claims 1-7, wherein the shaft further comprises a thread runout region proximal of the threadless atraumatic tip in which a thread height of the threads gradually increases moving in a proximal direction from the threadless atraumatic tip.

Example 9. The orthopedic bone screw of any example herein, particularly example 8, wherein: a diameter of the cylindrical portion of the threadless atraumatic tip is less than the minor diameter of the threads; and the minor diameter of the threads increases in the thread runout region from the diameter of the cylindrical portion of the threadless atraumatic tip to a specified minor diameter.

Example 10. The orthopedic bone screw of any example herein, particularly any one of examples 1-9, wherein the threadless atraumatic tip further comprises a fillet surface portion between the cylindrical portion and the round end portion.

Example 11. The orthopedic bone screw of any example herein, particularly example 10, wherein the round end portion of the threadless atraumatic tip comprises a spherical end surface.

Example 12. The orthopedic bone screw of any example herein, particularly example 11, wherein the fillet surface portion comprises a first radius, and the spherical end surface comprises a second radius that is greater than the first radius.

Example 13. The orthopedic bone screw of any example herein, particularly any one of examples 1-12, wherein: the threads of the shaft are first threads comprising a first thread pitch; the head further comprises second threads having a second thread pitch; and the second thread pitch is greater than the first thread pitch.

Example 14. The orthopedic bone screw of any example herein, particularly any one of examples 1-13, wherein the orthopedic bone screw is configured as a self-tapping bone screw and comprises cutting flutes formed in the threadless atraumatic tip and in the threads of the shaft.

Example 15. The orthopedic bone screw of any example herein, particularly example 14, further comprising a thread runout region proximal of the threadless atraumatic tip, and wherein the cutting flutes extend into the thread runout region.

Example 16. The orthopedic bone screw of any example herein, particularly example 12, wherein: the cutting flutes comprise a first radially extending surface and a second radially extending surface; the first radially extending surface comprises a flat surface portion in the threadless atraumatic tip and a curved surface portion in the thread runout region; and the second radially extending surface is flat in the threadless atraumatic tip and in the thread runout region, and is parallel or substantially parallel to a longitudinal axis of the orthopedic bone screw.

Example 17. The orthopedic bone screw of any example herein, particularly any one of examples 1-16, wherein the length of the cylindrical portion of the threadless atraumatic tip is 25% to 100% of a diameter of the cylindrical portion of the threadless atraumatic tip.

Example 18. The orthopedic bone screw of any example herein, particularly any one of examples 1-17, wherein a diameter of the cylindrical portion of the threadless atraumatic tip is ±5% of the minor diameter of the threads.

Example 19. A method, comprising driving an orthopedic bone screw according to any one of examples 1-18 into a bone.

Example 20. An orthopedic bone screw, comprising: a head; and a shaft extending from the head and comprising threads, the threads comprising a major diameter and a minor diameter; the shaft comprising a threadless atraumatic tip opposite the head, the threadless atraumatic tip comprising a cylindrical portion that is distal of the threads, and a round end portion that is distal of the cylindrical portion and forms a tip of the orthopedic bone screw; wherein at least the cylindrical portion of the threadless atraumatic tip comprises a plurality of cutting flutes.

Example 21. The orthopedic bone screw of any example herein, particularly example 20, further comprising a thread runout region proximal of the threadless atraumatic tip, and wherein the cutting flutes extend into the thread runout region.

Example 22. The orthopedic bone screw of any example herein, particularly example 20 or example 21, wherein a length of the cylindrical portion of the atraumatic tip is 25% to 150% of the major diameter of the threads.

Example 23. The orthopedic bone screw of any example herein, particularly any one of examples 20-22, wherein an overall length of the threadless atraumatic tip is 50% to 100% of a diameter of the cylindrical portion of the threadless atraumatic tip.

Example 24. The orthopedic bone screw of any example herein, particularly any one of examples 20-23, wherein the threads comprise a thread pitch, and the length of the cylindrical portion of the threadless atraumatic tip is 100% to 500% of the thread pitch.

Example 25. An orthopedic bone screw, comprising: a head; a shaft extending from the head, the shaft comprising threads; the shaft comprising a threadless atraumatic tip opposite the head, the threadless atraumatic tip comprising a cylindrical portion and a round end portion distal of the cylindrical portion; wherein the threadless atraumatic tip has a length that is 50% to 100% of a diameter of the cylindrical portion of the threadless atraumatic tip.

Example 26. The orthopedic bone screw of any example herein, particularly example 25, wherein the cylindrical portion of the threadless atraumatic tip has a length that is 25% to 100% of the diameter of the cylindrical portion of the threadless atraumatic tip.

Example 27. The orthopedic bone screw of any example herein, particularly example 25 or example 26, wherein a length of the cylindrical portion of the threadless atraumatic tip is 25% to 150% of a major diameter of the threads.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims and equivalents of the recited features. We therefore claim all that comes within the scope and spirit of these claims.

The invention claimed is:

1. An orthopedic bone screw, comprising:

a head; and a shaft extending from the head and comprising threads, the threads comprising a major diameter and a minor diameter;

the shaft comprising a threadless atraumatic tip opposite the head, the threadless atraumatic tip comprising a cylindrical portion that is distal of the threads, and a round end portion that is distal of the cylindrical portion and forms a tip of the orthopedic bone screw;

the shaft further comprising a thread runout region proximal of the threadless atraumatic tip in which a thread height of the threads gradually increases moving in a proximal direction from the threadless atraumatic tip;

wherein a length of the cylindrical portion of the threadless atraumatic tip is 25% to 150% of the major diameter of the threads, and the major diameter of the threads is measured proximally of the thread runout region;

wherein the threads comprise a thread pitch, and the length of the cylindrical portion of the threadless atraumatic tip is 100% to 500% of the thread pitch; and wherein a diameter of the cylindrical portion of the threadless atraumatic tip is 90% to 100% of the minor diameter of the threads.

2. The orthopedic bone screw of claim 1, wherein an overall length of the threadless atraumatic tip is 50% to 100% of a diameter of the cylindrical portion of the threadless atraumatic tip.

3. The orthopedic bone screw of claim 1, wherein:

the diameter of the cylindrical portion of the threadless atraumatic tip is less than the minor diameter of the threads; and the minor diameter of the threads increases in the thread runout region from the diameter of the cylindrical portion of the threadless atraumatic tip to a specified minor diameter.

4. The orthopedic bone screw of claim 1, wherein the threadless atraumatic tip further comprises a fillet surface portion between the cylindrical portion and the round end portion.

5. The orthopedic bone screw of claim 4, wherein the round end portion of the threadless atraumatic tip comprises a spherical end surface.

6. The orthopedic bone screw of claim 5, wherein the fillet surface portion comprises a first radius, and the spherical end surface comprises a second radius that is greater than the first radius.

7. The orthopedic bone screw of claim 1, wherein:

the threads of the shaft are first threads comprising a first thread pitch;

the head further comprises second threads having a second thread pitch; and the second thread pitch is greater than the first thread pitch.

8. The orthopedic bone screw of claim 1, wherein the orthopedic bone screw is configured as a self-tapping bone screw and comprises cutting flutes formed in the threadless atraumatic tip and in the threads of the shaft.

9. The orthopedic bone screw of claim 8, wherein the cutting flutes extend into the thread runout region.

10. The orthopedic bone screw of claim 9, wherein:

the cutting flutes comprise a first radially extending surface and a second radially extending surface;

the first radially extending surface comprises a flat surface portion in the threadless atraumatic tip and a curved surface portion in the thread runout region; and the second radially extending surface is flat in the threadless atraumatic tip and in the thread runout region, and is parallel or substantially parallel to a longitudinal axis of the orthopedic bone screw.

11. The orthopedic bone screw of claim 1, wherein the length of the cylindrical portion of the threadless atraumatic tip is 25% to 100% of a diameter of the cylindrical portion of the threadless atraumatic tip.

12. A method, comprising driving the orthopedic bone screw of claim 1 into a bone.

13. The orthopedic bone screw of claim 1, wherein an overall length of the threadless atraumatic tip is 200% to 600% of the thread pitch.

14. The orthopedic bone screw of claim 1, wherein the threads on the shaft are single lead threads, and the thread runout region comprises two threads to five threads.

15. The orthopedic bone screw of claim 10, wherein the second radially extending surface extends straight through the threadless atraumatic tip to the tip of the orthopedic bone screw, and forms an angle of 1° to 5° to the longitudinal axis of the orthopedic bone screw.

16. An orthopedic bone screw, comprising:

a head; and a shaft extending from the head and comprising threads, the threads comprising a major diameter and a minor diameter;

the shaft comprising a threadless atraumatic tip opposite the head, the threadless atraumatic tip comprising a cylindrical portion that is distal of the threads, and a round end portion that is distal of the cylindrical portion and forms a tip of the orthopedic bone screw;

wherein at least the cylindrical portion of the threadless atraumatic tip comprises a plurality of cutting flutes;

wherein the threads comprise a thread pitch, and a length of the cylindrical portion of the threadless atraumatic tip is 100% to 500% of the thread pitch; and wherein a diameter of the cylindrical portion of the threadless atraumatic tip is 90% to 100% of the minor diameter of the threads.

17. The orthopedic bone screw of claim 16, further comprising a thread runout region proximal of the threadless atraumatic tip, and wherein the cutting flutes extend into the thread runout region.

18. The orthopedic bone screw of claim 17, wherein the major diameter of the threads is measured proximally of the thread runout region, and the length of the cylindrical portion of the threadless atraumatic tip is 25% to 150% of the major diameter of the threads.

19. The orthopedic bone screw of claim 16, wherein an overall length of the threadless atraumatic tip is 50% to 100% of the diameter of the cylindrical portion of the threadless atraumatic tip.

20. The orthopedic bone screw of claim 16, wherein the length of the cylindrical portion of the threadless atraumatic tip is 100% to 500% 300% of the thread pitch.

21. An orthopedic bone screw, comprising:

a head;

a shaft extending from the head, the shaft comprising threads, the threads comprising a major diameter;

the shaft comprising a threadless atraumatic tip opposite the head, the threadless atraumatic tip comprising a cylindrical portion and a round end portion distal of the cylindrical portion;

the shaft further comprising a thread runout region proximal of the threadless atraumatic tip in which a thread height of the threads gradually increases moving in a proximal direction from the threadless atraumatic tip;

wherein the threadless atraumatic tip has a length that is 50% to 100% of a diameter of the cylindrical portion of the threadless atraumatic tip;

wherein a length of the cylindrical portion of the threadless atraumatic tip is 25% to 150% of the major diameter of the threads, and the major diameter of the threads is measured proximally of the thread runout region; and wherein the threads comprise a thread pitch, and the length of the cylindrical portion of the threadless atraumatic tip is 100% to 500% of the thread pitch.

22. An orthopedic bone screw, comprising:

a head; and a shaft extending from the head and comprising threads, the threads comprising a major diameter and a minor diameter;

the shaft comprising a threadless atraumatic tip opposite the head, the threadless atraumatic tip comprising a cylindrical portion that is distal of the threads, and a round end portion that is distal of the cylindrical portion and forms a tip of the orthopedic bone screw;

the shaft further comprising a thread runout region proximal of the threadless atraumatic tip in which a thread height of the threads gradually increases moving in a proximal direction from the threadless atraumatic tip;

wherein a length of the cylindrical portion of the threadless atraumatic tip is 25% to 150% of the major diameter of the threads, a diameter of the cylindrical portion of the threadless atraumatic tip is less than the minor diameter of the threads, and the minor diameter of the threads increases in the thread runout region from the diameter of the cylindrical portion of the threadless atraumatic tip to a specified minor diameter; and wherein the diameter of the cylindrical portion of the threadless atraumatic tip is 90% to 100% of the minor diameter of the threads.

* * * * *